United States Patent
Parry

(10) Patent No.: US 7,184,155 B2
(45) Date of Patent: Feb. 27, 2007

(54) IMAGE FORMING DEVICES AND METHODS OF OBTAINING MEDICATION INFORMATION

(75) Inventor: Travis J. Parry, Boise, ID (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1012 days.

(21) Appl. No.: 09/861,211

(22) Filed: May 18, 2001

(65) Prior Publication Data
US 2002/0171865 A1    Nov. 21, 2002

(51) Int. Cl.
G06F 3/12 (2006.01)
G06K 1/00 (2006.01)

(52) U.S. Cl. ........................ 358/1.15; 358/1.9; 358/1.6

(58) Field of Classification Search ............... 358/1.15, 358/1.9, 1.6, 1.13, 403; 700/231, 232, 233, 700/234, 235, 236, 237, 238, 214, 216; 709/224, 709/228, 319, 321; 710/7, 8, 19, 33, 46
See application file for complete search history.

(56) References Cited

U.S. PATENT DOCUMENTS

| | | | |
|---|---|---|---|
| 5,956,487 A | | 9/1999 | Venkatraman et al. |
| 6,068,156 A * | | 5/2000 | Liff et al. ...................... 221/7 |
| 6,442,449 B1 * | | 8/2002 | Blasy et al. ................. 700/235 |
| 6,480,292 B1 * | | 11/2002 | Sugiyama ................... 358/1.15 |
| 6,594,549 B2 * | | 7/2003 | Siegel ......................... 700/241 |
| 2001/0047281 A1 * | | 11/2001 | Keresman et al. .............. 705/2 |
| 2002/0029223 A1 * | | 3/2002 | Rice et al. ................ 707/104.1 |
| 2002/0052760 A1 * | | 5/2002 | Munoz et al. .................. 705/2 |
| 2002/0062230 A1 * | | 5/2002 | Morag et al. ................... 705/3 |
| 2002/0107824 A1 * | | 8/2002 | Ahmed ........................ 706/46 |
| 2002/0111832 A1 * | | 8/2002 | Judge ............................. 705/3 |
| 2002/0111873 A1 * | | 8/2002 | Ehrlich et al. ................. 705/26 |
| 2002/0169743 A1 * | | 11/2002 | Arnold et al. .................. 707/1 |
| 2003/0018495 A1 * | | 1/2003 | Sussman ........................ 705/2 |
| 2003/0158755 A1 * | | 8/2003 | Neuman ......................... 705/3 |

\* cited by examiner

*Primary Examiner*—Douglas Q. Tran

(57) ABSTRACT

Image forming devices and methods of obtaining medication information are described. According to one aspect, an image forming device includes: an input device configured to receive input information regarding a medication prescription for an individual; an interface adapted to communicate with a network external of the image forming device; and processing circuitry coupled with the input device and the interface and configured to receive the input information regarding the medication prescription from the input device and to forward a search request for a medication identified within the medication prescription to the interface for application to the network, and wherein the interface is configured to receive results of the search request from the network comprising search information regarding the medication; and an image engine coupled with the processing circuitry and configured to form a hard image upon media including the search information received from the network.

34 Claims, 2 Drawing Sheets

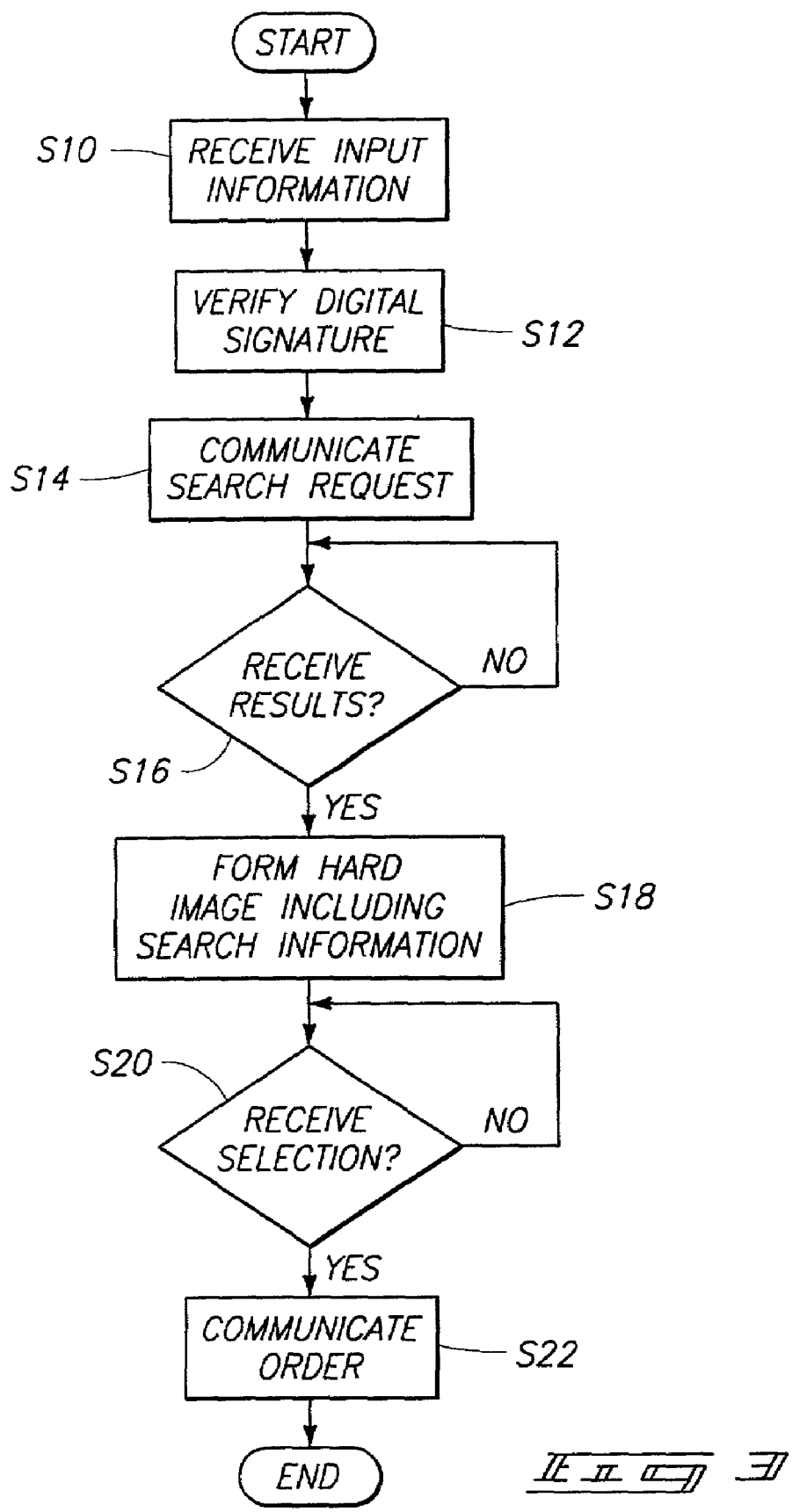

IMAGE FORMING DEVICES AND METHODS OF OBTAINING MEDICATION INFORMATION

FIELD OF THE INVENTION

This invention relates to image forming devices and methods of obtaining medication information.

BACKGROUND OF THE INVENTION

Receiving prescriptions and obtaining prescribed medications is a necessity for a large percentage of the population. Often, the process for ultimately filling the prescriptions may be burdensome, especially for the elderly or sick individuals. The pricing of medications prescribed may vary greatly depending upon where such medications are purchased. In addition, a given individual may need the prescribed medication immediately or in the short term. Such a person may not have the time to adequately research options to ascertain the best price for a given medication. Further, the person may not have access to information regarding the medication. Such people typically resort to proceeding to a known pharmacy wherein the pricing for the medication may not be the most attractive.

In addition, other inconveniences may be experienced wherein the person forgets to immediately order the medication, not have the required time to go to the pharmacy and wait for the medication to be prepared, etc.

Accordingly, there exists a need for improved devices and methodologies which assist with obtaining prescribed medications.

SUMMARY OF THE INVENTION

The invention provides image forming devices and methods of obtaining medication information.

According to one aspect of the invention, an image forming device includes: an input device configured to receive input information regarding a medication prescription for an individual; an interface adapted to communicate with a network external of the image forming device; and processing circuitry coupled with the input device and the interface and configured to receive the input information regarding the medication prescription from the input device and to forward a search request for a medication identified within the medication prescription to the interface for application to the network, and wherein the interface is configured to receive results of the search request from the network comprising search information regarding the medication; and an image engine coupled with the processing circuitry and configured to form a hard image upon media including the search information received from the network.

A second aspect of the invention includes a method of obtaining medication information comprising: receiving input information regarding a medication prescription for an individual within an image forming device; formulating a search request for a medication identified within the medication prescription using the image forming device; communicating the search request to a network coupled with the image forming device; receiving results including search information regarding the medication within the image forming device responsive to the communicating; and forming a hard image including the search information upon media using the image forming device.

Yet another embodiment of the invention provides a method of obtaining medication information comprising: receiving input information within a printer, the input information comprising a medication prescription for an individual, a digital signature associated with the medication prescription, payor information regarding the individual, and insurance information for the individual; verifying the digital signature using the printer; formulating a search request using the printer responsive to the verifying, the search request including an identification of medication within the medication prescription, the payor information and the insurance information; first communicating the search request using processing circuitry of the printer configured as an embedded web server to a network comprising the Internet coupled with the printer; receiving results including search information regarding the medication within the printer responsive to the first communicating, the results including a plurality of providers of the medication, price information of the medication for the respective providers, and insurance coverage for the respective providers; printing a hard image upon media including the search information using the printer; receiving a selection of at least one of the providers of the medication; and second communicating an order including the payor information, the insurance information, and the medication prescription to the selected at least one provider using the processing circuitry of the printer configured as an embedded web server.

Other features and advantages of the invention will become apparent to those of ordinary skill in the art upon review of the following detailed description, claims, and drawings.

DESCRIPTION OF THE DRAWINGS

FIG. 3 is a flowchart depicting an exemplary methodology for searching information regarding a medication.

DETAILED DESCRIPTION OF PREFERRED EMBODIMENTS

Figure 1:
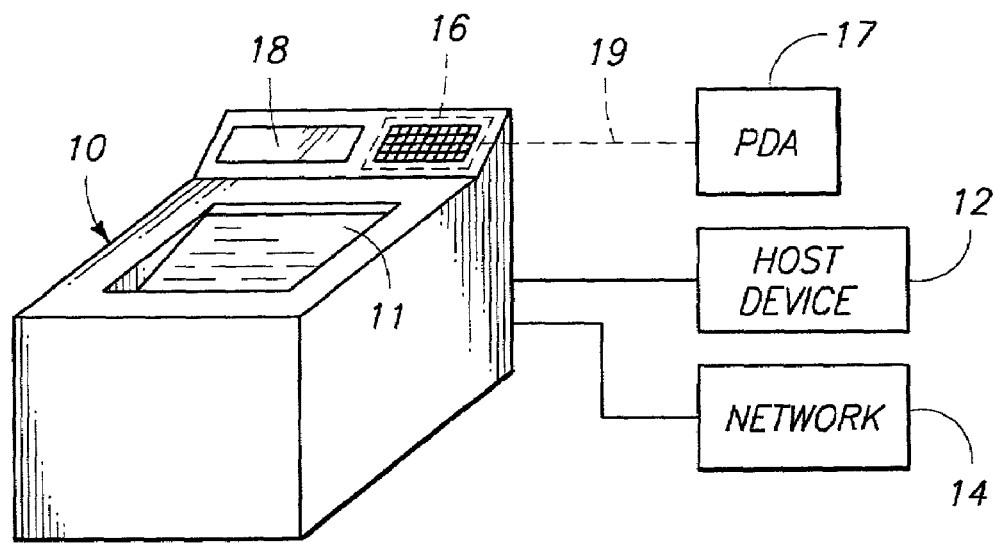
FIG. 1 is an illustrative representation of an exemplary image forming device.

Referring to FIG. 1, aspects of the present invention are described with reference to an image forming device 10. Image forming device 10 is configured to assist with obtaining information regarding medications and/or ordering of medications. In exemplary implementations, image forming device 10 of the present invention is provided within a kiosk conveniently located within a hospital, doctor's office, or other desired location. Other arrangements for device 10 are within the scope of the present invention.

The depicted image forming device 10 of FIG. 1 is implemented as a printer, such as a laser printer, inkjet printer, bubble jet printer, thermal printer, etc., in the described embodiment. Image forming device 10 may be implemented within other constructions according to other embodiments of the invention, some of which include other device configurations arranged to form hard images such as fax machines, multiple-function devices, etc.

Image forming device 10 is coupled with a host device 12 and a network 14 in the illustrated configuration. Host device 12 may be implemented as a personal computer including an Intel™ or Advanced Micro Devices (AMD)™ processor. According to one embodiment of the invention, host device 12 is optional inasmuch as image forming device 10 is configured to implement aspects of the invention described herein. Utilization of host device 12 may assist with expanding the functionality of image forming device 10.

Network 14 is coupled with image forming device 10 in the depicted arrangement. Network 14 represents a packet-switched network configured to communicate digital data in one exemplary embodiment, such as the Internet. Other configurations of network 14 are possible and include for example an intranet, private network, or any other arrangement configured to provide communication between a plurality of devices. Network 14 comprises a plurality of network devices (not shown) individually configured to communicate digital data within network 14. Exemplary network devices include personal computers, workstations, servers, routers, and other devices capable of communicating digital information. Image forming device 10 includes an appropriate interface (shown in FIG. 2) to implement bidirectional communications between image forming device 10 and network devices of network 14.

Image forming device 10 is operable to form hard images upon media 11 in the illustrated embodiment. Exemplary media 11 includes sheet or roll media, such as paper, labels, transparencies, etc., and other media capable of being imaged upon. Media 11 may be formatted as a brochure to provide a convenient detailed report of medication information to users in accordance with aspects of the present invention.

As shown in the illustrated configuration, image forming device 10 includes an input device 16 and a display 18. Input device 16 enables a user or other entity to provide commands and/or data into image forming device 10. An exemplary input device 16 include a key pad to receive manually input information and/or a data port configured to implement electronic transfer of files, data and/or commands. The data port of input device 16 is configured to communicate digital data via a communication medium 19 in the described embodiment. An example of medium 19 is an infrared coupling. For example, a user or other entity may be provided with a digital data communication device 17, such as a personal digital assistant (PDA). Communication device 17 is configured to transmit and receive data, commands and/or files with respect to input device 16 of image forming device 10.

Display 18 comprises a liquid crystal display (LCD) in but one example. Display 18 is operational to indicate status of image forming device 10, alarm conditions, and other desired information for conveyance to the user. Such information may also be communicated to communication device 17 or provided upon media 11.

As described below, image forming device 10 is configured to assist with ordering medication pursuant to a prescription from a physician or other authorized party. Image forming device 10 is configured to access network 14 to retrieve information regarding a specific medication and to provide such information in hard image form upon media 11 for use by individuals. The present invention encompasses other aspects as described herein.

Figure 2:
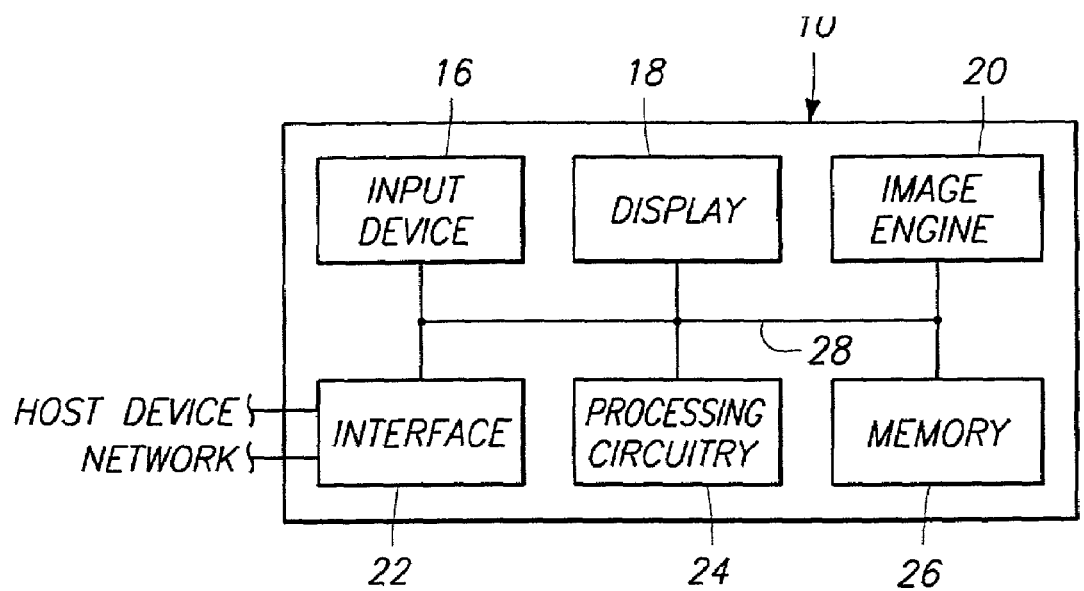
FIG. 2 is a functional block diagram of components of an exemplary image forming device.

Referring to FIG. 2, further details of image forming device 10 are depicted. In addition to features described above, image forming device 10 additionally includes an image engine 20, an interface 22, processing circuitry 24 and memory 26. A bus 28 is provided to implement communications intermediate input device 16, display 18, image engine 20, interface 22, processing circuitry 24, and memory 26.

The depicted configuration of image forming device 10 is exemplary to illustrate aspects of the present invention and other components and/or functionality may be provided within device 10 according to other embodiments of the invention. In particular, some of the depicted components are optional and other arrangements of image forming device 10 configured to form hard images are possible. The exemplary embodiment disclosed herein is discussed with reference to a printer application although the present invention applies to other configurations.

Input device 16 is configured to receive input information regarding a medication prescription for an individual. Such medication prescription typically identifies the medication, the dosage, days supply, refill information, expiration information and the patient to receive the medication. In addition, a digital signature may be provided with the medication prescription and which is associated with a prescribing physician. The digital signature may be utilized by image forming device 10 to verify the authenticity of the received medication prescription. Digital signature functionality may be implemented using RSA technology, for example. Other verification arrangements may be utilized.

The verification of digital signatures using the appropriate technology may be utilized to control the generation of search requests and forwarding of search requests. If the digital signature is deemed to be authentic, processing circuitry 24 proceeds to formulate and forward one or more search request to interface 22 for communication to network 14 in one embodiment. If the digital signature is not indicated to be authentic, processing circuitry 24 suspends or does not initiate search operations with respect to the received medication prescription and can take further desired actions such as requesting confirmation of the inputted digital signature, for example.

Inclusion of digital signatures or authentication of digital signatures may also be utilized to control ordering of medications. For example, any user may be able to initiate search operations to receive medication information using device 10 while only those with authenticated digital signatures can order medications using device 10 as discussed below. Other operations are possible.

Input information received via input device 16 may also include payor information regarding an individual who is financially responsible for the medication prescribed within the medication prescription. The payor information identifies the individual, an appropriate account to obtain funds for payment of the medication (e.g., a credit card number), expiration date, and/or other information necessary to implement payment for the medication.

Insurance information corresponding to the individual to receive the medication may also be provided via input device 16 to facilitate the location of an appropriate provider, also referred to as a supplier (e.g., pharmacy, manufacturer, retailer, etc.) of the medication who honors the particular type of insurance. For example, the insurance information may include the appropriate vendor and identification number for the appropriate individual. The insurance information is utilized to obtain insurance coverage information for the medication to facilitate ordering of the prescription.

Image engine 20 implements formation of hard images upon media 11. In the described embodiment wherein image forming device 10 comprises a printer, image engine 20 is implemented as a print engine. An exemplary print engine includes a developing assembly and a fusing assembly (not shown) to respectively form images using developing material and to affix the developing material to media 11. Other constructions or embodiments of image engine 20 are possible.

Interface 22 is configured to communicate with devices external of device 10. Interface 22 is implemented in different configurations depending upon the application of image forming device 10. For example, interface 22 comprises a network interface card (NIC) and/or an appropriate modem for communicating with external devices, such as network devices within network 14. Further, interface 22 may additionally include a parallel or other connection to implement communications with host device 12.

Processing circuitry 24 is configured to execute executable instructions to control operations of image forming device 10. For example, processing circuitry 24 controls image engine 20 to implement imaging operations. Processing circuitry 24 is configured to execute executable instructions stored within memory 24 and comprising for example, software and/or firmware instructions.

In the described embodiment, memory 26 includes executable code to configure processing circuitry 24 as an embedded web server (EWS) which communicates with host device 12 and/or devices of network 14. Embedded web server concepts are described in U.S. Pat. No. 5,956,487, incorporated herein by reference. Such functionality enables processing circuitry 24 to communicate with host device 12 and/or network devices of network 14, to forward search requests to such devices, to receive search results, to serve up web pages, etc. Exemplary processing circuitry 24 comprises a microprocessor.

Memory 26 stores digital information and instructions. For example, memory 26 is configured to store image data to be imaged using image engine 20, executable instructions usable by processing circuitry 24 to implement imaging operations and control operations of image forming device 10, as well as other digital data to be stored within image forming device 10. Memory 26 comprises random access memory, read only memory, flash memory, and/or a disk drive, in one example.

Image forming device 10 is arranged to assist with obtaining information regarding one or more medication prescribed within a medication prescription and/or placing an order for one or more medication. Processing circuitry 24 receives the input information received via input device 16 regarding the medication prescription. In the described embodiment, processing circuitry 24 is arranged to formulate a search request for one or more medication identified within the medication prescription.

For example, processing circuitry 24 implemented to function as an embedded web server as described herein operates to search network 14 by formulating appropriate search requests. An exemplary search request includes an e-mail or other electronic query communicated to appropriate recipients which may be identified within memory 26 corresponding to providers of the desired medication. In such an embodiment, memory 26 includes a plurality of identifiers of appropriate devices within network 14 corresponding to manufacturers or suppliers of the medication. Exemplary identifiers of network devices of network 14 include e-mail addresses, uniform resource locators (URLs), or other appropriate identifiers. Identifiers may also be inputted by a user upon input device 16.

Alternatively, processing circuitry 24 embodied as an embedded web server in the described embodiment searches network 14 to identify providers of the medication and associated information regarding the medication. Processing circuitry 24 formulates the search request for the medication identified within the medication prescription. The search request may request identification of providers of the medication as well as information regarding the medication. In addition, processing circuitry 24 may include insurance information and/or payor information within the search request if provided by the individual. Payor and insurance information may be included within the search request if desired to verify acceptance by the providers of the method of payment and insurance indicated within the search request.

As mentioned above, processing circuitry 24 may formulate a search request to obtain information regarding one or more medication. Such desired information can include price information, acceptance of payment method, acceptance of insurance, directions, precautions, claimed benefits, etc. Processing circuitry 24 forwards a search request to a provider of the medication identified within the inputted information, identified in memory 26, or otherwise identified in network 14 in one instance.

Following formulation of the search request by processing circuitry 24 in the described embodiment, processing circuitry 24 forwards the search request to interface 22 for communication to appropriate external devices such as host device 12 or devices within network 14. It may be desirable to include more than one medication (if needed by the user) to receive favorable pricing for multiple medications (if such is available by a provider of the medications). The described searching operations are exemplary and other searching methods for retrieving medication information are possible.

Following submission of the search request to interface 22, image forming device 10 awaits reception of results to the search request. In the described exemplary embodiment, the results of the search request are received within interface 22 from the appropriate external device(s) including host device 12 and/or devices of network 14.

The results of the search request include search information regarding the medication. For example, the search information includes one or more provider of the medication. The search information may additionally include price information of the medication for the respective providers. Further, information from the manufacturer of the medication or other source may also be received responsive to an appropriate search request as described above.

If insurance information is provided by the individual, the search information may also include an insurance verification report identifying the respective providers of the medication and respective insurance coverage of the medication by the providers. For example, the search information can include whether or not coverage is provided, the appropriate co-pay for the medication, and other relevant information with respect to insurance coverage. Further, acceptance of the payment method indicated by payor information may be indicated for the respective providers. If more than one medication is included in the search request, the aforementioned search information includes information for all of the medications if available by the providers in accordance with one embodiment.

Following receipt of the search results including the search information, processing circuitry 24 is arranged to control image engine 20 to form hard images upon media 11 utilizing the search information according to one aspect. Processing circuitry 24 controls display 18 to depict the results including the search information according to another aspect. Further, a message including the search information may be communicated externally of device 10 to appropriate recipients, such as the individual needing the medication. The search information may be communicated in a brochure format or other attractive format to conveniently and accurately display options for the individual purchasing the medication. Image forming device 10 may forward the search information to an external device including host device 12 or a device of network 14 via an appropriate message such as an e-mail message.

According to additional aspects of the invention, input device 16 is also operable to receive a selection of at least one of the identified providers. Responsive to the selection, processing circuitry 24 is arranged in one exemplary embodiment to formulate an order and to forward the order to interface 22 for communication to the selected provider. The order may be embodied within an appropriate e-mail message or other desired electronic message for communication to the provider. If desired, processing circuitry 24 may include payor and/or insurance information within the order as received from input device 16. Thereafter, the provider forwards the medication to an address of the individual following receipt of the order.

Referring to FIG. 3, an exemplary methodology performed by image forming device 10 is illustrated. The illustrated methodology depicts exemplary aspects of the invention and other methods are encompassed within the present invention. Executable code for implementing the methodology of FIG. 3 is provided within memory 26 in the described embodiment. Processing circuitry 24 executes such code to implement the depicted methodology. Other embodiments or implementations are possible.

Referring initially to a step S10, processing circuitry 24 access input information received within image forming device 10. Exemplary input information includes a medication prescription, an identification of the individual to receive the medication prescription, a digital signature associated with the medication prescription, payor information regarding the individual and/or insurance information regarding the individual as described above.

At a step S12, processing circuitry 24 verifies the digital signature using the appropriate technology. For example, processing circuitry 24 may utilize a public key to verify the contents of the input information.

At a step S14, processing circuitry 24 formulates a search request formatted for communication to network 14. The search request includes inputted information for use by network devices of network 14 to implement an appropriate search of network 14 for information regarding the medication.

At a step S16, processing circuitry 24 awaits the reception of results to the search request from network 14. Processing circuitry 24 idles at step S16 or performs other operations until the appropriate results are received.

At a step S18, processing circuitry 24 formats the results for communication to a user. In accordance with some aspects of the present invention, processing circuitry 24 formats received data for utilization within image engine 20. Image engine 20 prints the received results upon media 11 for use by the individual or other user. The received information regarding the medication may be communicated in other convenient methods to the individual, including using display 18, e-mail, etc.

At a step S20, processing circuitry 24 monitors for the reception of a selection via input device 16. For example, after reviewing the printed materials upon media 11, the individual may place a selection using input device 16. Processing circuitry 24 idles at step S20 or performs other operations until a selection of a provider is received. Alternatively, processing circuitry 24 may end the methodology if a time out period is experienced.

Responsive to the reception of an appropriate selection, processing circuitry 24 proceeds to a step S22 to communicate the order according to the selection. Processing circuitry 24 forwards the order to interface 22 for communication to the appropriate network device within network 14 identified as a provider of the medication and as selected by the user in step S20.

The protection sought is not to be limited to the disclosed embodiments, which are given by way of example only, but instead is to be limited only by the scope of the appended claims.

What is claimed is:

1. An image forming device comprising:
   an input device configured to receive input information regarding a medication prescription for an individual;
   an interface adapted to communicate with a network external of the image forming device; and
   processing circuitry coupled with the input device and the interface and configured to receive the input information regarding the medication prescription from the input device and to forward a search request for a provider of a medication identified within the medication prescription to the interface for application to the network, and wherein the interface is configured to receive results of the search request from the network comprising search information regarding the medication; and
   an image engine coupled with the processing circuitry and configured to form a hard image upon media including the search information received from the network.

2. The device in accordance with claim 1 wherein the interface is configured to receive the results including the search information comprising at least one provider of the medication, and wherein the processing circuitry is configured to control the image engine to form the hard image comprising the at least one provider of the medication.

3. The device in accordance with claim 1 wherein the interface is configured to receive the results including the search information comprising at least one provider of the medication and respective price information of the medication for the at least one provider, and wherein the processing circuitry is configured to control the image engine to form the hard image comprising the at least one provider of the medication and the respective price information of the medication for the at least one provider.

4. The device in accordance with claim 1 wherein the input device is configured to receive a selection of at least one of a plurality of providers of the medication identified within the search information, and wherein the processing circuitry is configured to formulate an order responsive to the selection and to forward the order to the interface for communication to the at least one selected provider.

5. The device in accordance with claim 4 wherein the input device is configured to receive the input information comprising payor information regarding the individual associated with the prescription and the processing circuitry is configured to include the payor information within the order.

6. The device in accordance with claim 1 wherein the input device is configured to receive the input information comprising insurance information regarding the individual, and the processing circuitry is configured to forward the search request including the insurance information to the interface, and the interface is configured to receive the results including search information comprising at least one provider of the medication and associated insurance coverage with respect to the at least one provider.

7. The device in accordance with claim 1 wherein the input information includes a digital signature associated with the medication prescription and the processing circuitry is configured to verify the digital signature and to forward the search request responsive to the verification.

8. The device in accordance with claim 1 further comprising a display configured to depict the results comprising the search information.

9. The device in accordance with claim 1 wherein the image engine comprises a print engine configured to print hard images.

10. The device in accordance with claim 1 wherein the interface is configured to communicate with the network comprising the Internet and the processing circuitry comprises an embedded web server configured to communicate with the Internet.

11. The device in accordance with claim 1 wherein the search information comprises a plurality of providers individually capable of providing the medication of the medication prescription to the individual.

12. The device in accordance with claim 11 wherein the providers comprise different entities not affiliated with one another.

13. The device in accordance with claim 1 wherein the interface is adapted to communicate with a plurality of entities coupled with the network and not affiliated with the image forming device.

14. The device in accordance with claim 1 further comprising a housing, and wherein the input device, the interface, the processing circuitry and the image engine are provided within the housing.

15. The device in accordance with claim 1 wherein the processing circuitry is configured to formulate the search request to search for a provider having a lowest price for the medication identified within the medication prescription.

16. The device in accordance with claim 1 wherein the search information identifies a plurality of possible providers of the medication identified within the medication prescription, and the input device is configured to receive a selection of one of the providers.

17. The device in accordance with claim 1 further comprising storage circuitry configured to store electronic addresses for a plurality of providers of the medication, and wherein the processing circuitry is configured to formulate the search request comprising an e-mail communication addressed to the providers using the electronic addresses stored in the storage circuitry.

18. A method of obtaining medication information comprising:
receiving input information regarding a medication prescription for an individual within an image forming device;
formulating a search request for price information of a plurality of providers for a medication identified within the medication prescription using the image forming device;
communicating the search request to a network coupled with the image forming device;
receiving results including search information regarding the medication within the image forming device responsive to the communicating; and
forming a hard image including the search information upon media using the image forming device.

19. The method in accordance with claim 18 wherein the receiving comprises receiving the results including the search information comprising at least one provider of the medication, and the forming comprises forming the hard image comprising the at least one provider of the medication.

20. The method in accordance with claim 18 wherein the receiving comprises receiving the results including the search information comprising at least one provider of the medication and respective price information of the medication for the at least one provider, and the forming comprises forming the hard image comprising the at least one provider of the medication and respective price information of the medication for the at least one provider.

21. The method in accordance with claim 18 further comprising:
receiving a selection of at least one of a plurality of providers of the medication; and
communicating an order to the at least one selected provider using the image forming device.

22. The method in accordance with claim 21 further comprising receiving payor information regarding the individual, and wherein the communicating the order comprises communicating the payor information within the order.

23. The method in accordance with claim 18 further comprising:
receiving insurance information regarding the individual;
forwarding the insurance information to the network; and
receiving information identifying at least one provider of the medication and respective insurance coverage of the medication for the at least one provider.

24. The method in accordance with claim 18 wherein the receiving input information comprises receiving a digital signature associated with the medication prescription, and further comprising verifying the digital signature, and wherein the communicating is responsive to the verifying.

25. The method in accordance with claim 18 further comprising displaying the results comprising the search information using a display.

26. The method in accordance with claim 18 wherein the forming the hard image comprises printing the hard image.

27. The method in accordance with claim 18 wherein the communicating comprises communicating the search request to the network comprising the Internet using processing circuitry of the image forming device configured as an embedded web server.

28. The method in accordance with claim 18 wherein the search information comprises a plurality of providers individually capable of providing the medication of the medication prescription to the individual.

29. The method in accordance with claim 28 wherein the providers comprise different entities not affiliated with one another.

30. The method in accordance with claim 18 wherein the communicating comprises communicating the search request to a plurality of entities coupled with the network and not affiliated with the image forming device.

31. The method in accordance with claim 18 wherein the forming comprises forming the hard image including the search information comprising information regarding a provider having a lowest price for the medication identified within the medication prescription and the price for the medication.

32. The method in accordance with claim 18 wherein the receiving comprises receiving the results including search information which identifies a plurality of providers of the medication identified within the medication prescription, and further comprising receiving a selection of one of the providers after the forming the hard image.

33. The method in accordance with claim 18 wherein the formulating comprises formulating the search request comprising an e-mail communication.

34. A method of obtaining medication information comprising:
- receiving input information within a printer, the input information comprising a medication prescription for an individual, a digital signature associated with the medication prescription, payor information regarding the individual, and, insurance information for the individual;
- verifying the digital signature using the printer;
- formulating a search request using the printer responsive to the verifying, the search request including an identification of medication within the medication prescription, the payor information and the insurance information;
- first communicating the search request using processing circuitry of the printer configured as an embedded web server to a network comprising the Internet coupled with the printer;
- receiving results including search information regarding the medication within the printer responsive to the first communicating, the results including a plurality of providers of the medication, price information of the medication for the respective providers, and insurance coverage for the respective providers;
- printing a hard image upon media including the search information using the printer;
- receiving a selection of at least one of the providers of the medication; and
- second communicating an order including the payor information, the insurance information, and the medication prescription to the selected at least one provider using the processing circuitry of the printer configured as an embedded web server.

* * * * *

UNITED STATES PATENT AND TRADEMARK OFFICE
CERTIFICATE OF CORRECTION

PATENT NO. : 7,184,155 B2
APPLICATION NO. : 09/861211
DATED : February 27, 2007
INVENTOR(S) : Travis J. Parry It is certified that error appears in the above-identified patent and that said Letters Patent is hereby corrected as shown below:

In column 8, line 55, in Claim 5, delete "pavor" and insert -- payor --, therefor.

In column 11, line 7, in Claim 34, after "and" delete ",".

Signed and Sealed this

Eighteenth Day of August, 2009

David J. Kappos
*Director of the United States Patent and Trademark Office*